US012539158B2

(12) United States Patent
Santos et al.

(10) Patent No.: US 12,539,158 B2
(45) Date of Patent: Feb. 3, 2026

(54) SURGICAL IMPACTOR

(71) Applicant: Pro-Dex, Inc., Irvine, CA (US)

(72) Inventors: Daniel Manuel Santos, Irvine, CA (US); Justin Taber, Irvine, CA (US)

(73) Assignee: PRO-DEX, INC., Irvine, CA (US)

(*) Notice: Subject to any disclaimer, the term of this patent is extended or adjusted under 35 U.S.C. 154(b) by 329 days.

(21) Appl. No.: 18/181,144

(22) Filed: Mar. 9, 2023

(65) Prior Publication Data

US 2023/0285062 A1 Sep. 14, 2023

Related U.S. Application Data

(60) Provisional application No. 63/269,144, filed on Mar. 10, 2022.

(51) Int. Cl.
*A61B 17/92* (2006.01)

(52) U.S. Cl.
CPC ........ *A61B 17/92* (2013.01); *A61B 2017/924* (2013.01)

(58) Field of Classification Search
CPC . A61B 17/92; A61B 17/921; A61B 2017/922; A61B 2017/924; A61B 2017/925; A61B 2017/927; A61B 2017/928; A61F 2/46; A61F 2002/4681; A61F 2002/4683; A61F 2002/4688; A61F 2002/4689; A61F 2002/4698
See application file for complete search history.

(56) References Cited

U.S. PATENT DOCUMENTS

| | | | | |
|---|---|---|---|---|
| 9,364,345 | B2 | 6/2016 | Lloyd et al. | |
| 9,468,538 | B2 | 10/2016 | Nycz et al. | |
| 9,687,287 | B2 | 6/2017 | Hoeppner | |
| 9,775,724 | B2 | 10/2017 | Blaylock et al. | |
| 9,999,518 | B2 * | 6/2018 | Mani | A61F 2/4637 |
| 10,342,591 | B2 * | 7/2019 | Pedicini | B25D 11/068 |
| 11,197,706 | B2 * | 12/2021 | Pedicini | A61F 2/4603 |
| 11,413,083 | B2 | 8/2022 | Smith et al. | |
| 2003/0236523 | A1 | 12/2003 | Johnson et al. | |
| 2013/0261681 | A1 * | 10/2013 | Bittenson | A61B 17/92 606/86 R |

(Continued)

FOREIGN PATENT DOCUMENTS

| | | | | | |
|---|---|---|---|---|---|
| AU | 2023231283 | A1 * | 9/2024 | A61B 17/1628 |
| CN | 118922157 | A * | 11/2024 | A61B 17/1628 |

(Continued)

OTHER PUBLICATIONS

International Search Report and Written Opinion in corresponding International Patent Application No. PCT/US2023/064049, mailed May 11, 2023, in 29 pages.

*Primary Examiner* — Eric S Gibson
(74) *Attorney, Agent, or Firm* — Knobbe, Martens, Olson & Bear, LLP

(57) ABSTRACT

Various surgical impactors are disclosed. The surgical impactor may include a housing, a rod that extends at least partially inside the housing, a hammer head attached to the rod, and a hammer housing that receives the hammer head. Actuation of the rod can cause the hammer head to move proximally and/or distally inside, and to impact, the hammer housing. The force of the impact can be conveyed to a surgical implant, instrument, etc.

20 Claims, 12 Drawing Sheets

(56) References Cited

U.S. PATENT DOCUMENTS

| | | | | |
|---|---|---|---|---|
| 2014/0318819 | A1* | 10/2014 | Pedicini | A61B 17/1604 173/2 |
| 2014/0318823 | A1* | 10/2014 | Pedicini | A61B 17/1628 173/201 |
| 2015/0196343 | A1* | 7/2015 | Donald | A61B 17/92 606/100 |
| 2016/0199199 | A1* | 7/2016 | Pedicini | A61B 17/92 606/100 |
| 2017/0196704 | A1* | 7/2017 | Behzadi | A61F 2/4609 |
| 2019/0282286 | A1* | 9/2019 | Pedicini | B25D 11/125 |
| 2020/0008774 | A1 | 1/2020 | Behzadi | |
| 2020/0275967 | A1* | 9/2020 | Loftus-Vergari | B23B 31/1215 |
| 2021/0212701 | A1* | 7/2021 | Khosla | A61B 17/1615 |
| 2021/0251676 | A1* | 8/2021 | Wahl | A61B 17/162 |
| 2022/0054179 | A1* | 2/2022 | Pedicini | B25D 11/068 |
| 2022/0226033 | A1* | 7/2022 | Slocum | A61F 2/4603 |
| 2022/0361897 | A1* | 11/2022 | Chen | A61B 17/1631 |
| 2023/0285062 | A1* | 9/2023 | Santos | A61B 17/92 |

FOREIGN PATENT DOCUMENTS

| | | | | |
|---|---|---|---|---|
| EP | 3215042 | A1 | 9/2017 | |
| EP | 3253336 | A1 | 12/2017 | |
| WO | WO 1988/002246 | A2 | 4/1988 | |
| WO | WO 2022/074394 | A2 | 4/2022 | |
| WO | WO-2022182772 | A1 * | 9/2022 | A61B 17/1624 |
| WO | WO-2023173022 | A1 * | 9/2023 | A61B 17/1628 |

* cited by examiner

SURGICAL IMPACTOR

CROSS REFERENCE

This application claims priority to U.S. Provisional Patent Application No. 63/269,144, filed Mar. 10, 2022, which is hereby incorporated by reference in its entirety. All applications for which a foreign or domestic priority claim is identified in the Application Data Sheet as filed herewith are hereby incorporated by reference under 37 CFR 1.57.

BACKGROUND

Field

The present disclosure relates generally to a surgical impactor for medical procedures, such as a hammer energized by a linear actuator.

Description of Certain Related Art

Impactors are devices that provide impact force, which is a high force or shock applied over a short period to a discrete area. Impactors can be used in various medical procedures. For example, impactors can be used during surgery to assist in bone preparation, implant assembly, implant and/or bone graft installation, etc.

SUMMARY OF CERTAIN EMBODIMENTS

Some battery-powered automatic orthopedic impactors were specifically developed for hip replacement surgery and provide forward or reverse impacts through conversion of rotary motion from an electric motor to a pneumatic actuator. Some disadvantages of this device are the size and weight to support the motor and mechanism, as well as reliability issues due to requiring many moving parts within the mechanism that must be lubricated while also being autoclavable.

There is a need for an improved surgical impactor, such as an impactor that can controllably vary the impact energy, frequency, and/or direction of impacts. The optimal impact energy for broaching of bone or insertion of an implant into the bone varies depending on bone density. A patient with hard, dense bone may require additional impact energy to advance the instrument or implant. A patient with softer, more porous bone requires less impact energy to advance the device. Application of excessive impact energy in this case may excessively advance the device and cause injury to the patient if the instrument or implant fractures the bone or encroaches on adjacent neurovascular structures. An excessive and less controllable rate of displacement upon impact may cause harm to a patient, such as because the implant is more likely to be malpositioned and lead to anatomic misalignment. In some instances, it is safer and more effective to provide more impacts of smaller force, compared to fewer impacts of larger force. The ability to variably increase impact energy, frequency, and/or direction allows for more numerous and/or smaller impacts to advance the instrument or implant at an appropriate rate that can be effectively more continuous and controllable, improve accuracy in placement, reduce the chance of harm to the patient, and/or provide other benefits.

A variety of orthopedic procedures could benefit from the improved safety and precision of an adjustable automatic impactor. Some of these include: joint replacement surgery (e.g., total hip and total knee), orthopedic trauma intramedullary nail insertion (e.g., femoral, tibial, humeral, trochanteric), spine fusion interbody insertion (e.g., T/PLIF, ALIF, Lateral) and sacroilliac joint fusion, and sports medicine suture anchor insertion. Many of these procedures do not typically use automatic impaction. It may be difficult to justify the cost and risk to develop an impactor that is specialized for each of these applications. An impactor that can deliver a range of impact energies and frequencies has the potential to be utilized in multiple procedures, to provide efficiencies (e.g., in terms of ordering, maintaining, stocking, training, etc.), and/or to better support the upfront cost of development and initial production.

The impactor of the present disclosure seeks to address one or more of the concerns mentioned above, or other concerns. The impactor can be configured to provide forward or reverse impact force to tissue (e.g., bone), an instrument, or an implant. The force can be controlled and/or adjusted. In some implementations, the force is provided by linear acceleration of an internal hammer that collides with forward and reverse limits of travel within the device. The electromagnetic control of the hammer actuation allows for variable and independent control of impact energy, frequency, and direction.

The linear acceleration can be provided by a linear actuator, such as a linear magnetic actuator. The linear actuator can drive a central rod that makes forward or reverse impacts within a distal housing. These forward or reverse impacts are transferred through the distal shaft to the impact or instrument receiving impacts. In some embodiments, the direction of impact can be electronically controlled by adjusting the stroke of the oscillating magnet relative to the distal impact housing so that either forward or reverse impacts occur. In some embodiments, the rod can be removed from the linear actuator.

The linear actuator and impact mechanism may be housed within a surgical handpiece. The handpiece may include a housing, grip (e.g., pistol grip), detachable battery, controls, and/or outputs. The handpiece may feature interchangeable attachment points for integration with navigation or mounting to a surgical robotic arm.

Certain aspects of the present disclosure include a surgical impactor. The surgical impactor can include a housing. The housing can include a proximal end, a distal end, and a cavity. The cavity can extend between the proximal end and the distal end. The surgical impactor can include a rod. The rod can include a proximal end and a distal end. In some implementations, the rod can be removably disposed inside the cavity of the housing. In some aspects, the surgical impactor includes a hammer head on the distal end of the rod. In some implementations, the surgical impactor includes a hammer housing. The hammer housing can have a proximal end with a first opening, a distal end with a second opening, and a cavity disposed between the first and second openings. In some implementations, the surgical impactor includes an adapter. The adapter can have a proximal end and a distal end. The proximal end of the adapter can be attached to the distal end of the hammer housing. The hammer head can be positioned inside the cavity of the hammer housing and can move relative to the hammer housing. In some implementations, the surgical impactor includes a linear actuator. In some aspects, the linear actuator can move the rod, which can cause the hammer head to move axially inside the hammer housing and to impact an inner surface of the hammer housing.

In some aspects, the distal end of the adapter can be removably attached to a surgical implement. The surgical implement can include, for example, a surgical nail and/or a surgical staple. In some implementations, the surgical impactor can include one or more sensors. The one or more sensors can include at least one of an accelerometer, a force gauge sensor, and/or a displacement sensor. The linear actuator can include a magnetic linear actuator. The actuator can include a u-channel linear motor, a flat linear motor, a voice coil actuator (VCA), a moving coil actuator, and/or a solenoid. In some aspects, the surgical impactors can include a controller. The controller can control operational settings of the surgical impactor. The controller can include a processor and/or a memory. The operational settings of the surgical impactor can include at least one of an impact frequency, an impact direction, and/or an impact force. In some implementations, the hammer housing can include at least one window. The window can extend axially along the hammer housing. The hammer head can be visible through the at least one window of the hammer housing. In some implementations, the distal end of the rod can include a distal tip with a thread. The proximal end of the hammer head can include a threaded recess. The thread of the distal tip and the threaded recess can engage the rod to the hammer head. The surgical impactor can include a power source. The power source can can be positioned on an exterior of the housing. The power source can include a battery. In some implementations, an outer diameter of the hammer head can be greater than an outer diameter of the proximal end of the rod. The cavity of the housing can be unobstructed when the rod is not disposed inside the cavity.

Certain aspects of the present disclosure include a surgical handpiece. The surgical handpiece can include a grip. The surgical handpiece can include a trigger which can be positioned along the grip. The surgical handpiece can include a barrel connected to the grip. The barrel can include a cavity. The surgical handpiece can include a surgical impactor. The surgical impactor can be positioned inside the cavity of the barrel. In some implementations, the surgical impactor can include a housing. The housing can include a through-lumen. The surgical impactor can include a rod. The rod can be positioned at least partially in the through-lumen of the housing. The surgical impactor can include a hammer head. The hammer head can be positioned on an end of the rod. The surgical impactor can include a hammer housing. The hammer housing can receive the hammer head. The surgical impactor can include a linear actuator. The linear actuator can move the rod relative to the housing and/or dampen impact force from being transferred from the rod to the housing. The surgical impactor can include an electronic controller. The electronic controller can control operation of the linear actuator at least partly in response to actuation of the trigger.

In some aspects, actuation of the trigger can cause the hammer head to move axially in at least one of a proximal and distal direction inside the hammer housing. The linear actuator can include a magnetic linear actuator. In some implementations, the surgical handpiece can include a controller which can control operational settings of the surgical handpiece. The controller can include an electronic processor and a memory. The operational settings of the surgical handpiece can include at least one of an impact frequency, an impact direction, and/or an impact force.

DETAILED DESCRIPTION OF CERTAIN EMBODIMENTS

Various features and advantages of the disclosed technology will become more fully apparent from the following description of the embodiments illustrated in the figures. These embodiments are intended to illustrate the principles of this disclosure. However, this disclosure should not be limited to only the illustrated embodiments. The features of the illustrated embodiments can be modified, combined, removed, and/or substituted as will be apparent to those of ordinary skill in the art upon consideration of the principles disclosed herein. No features, structure, or step disclosed herein is essential or indispensable.

Overview

Figure 1A:
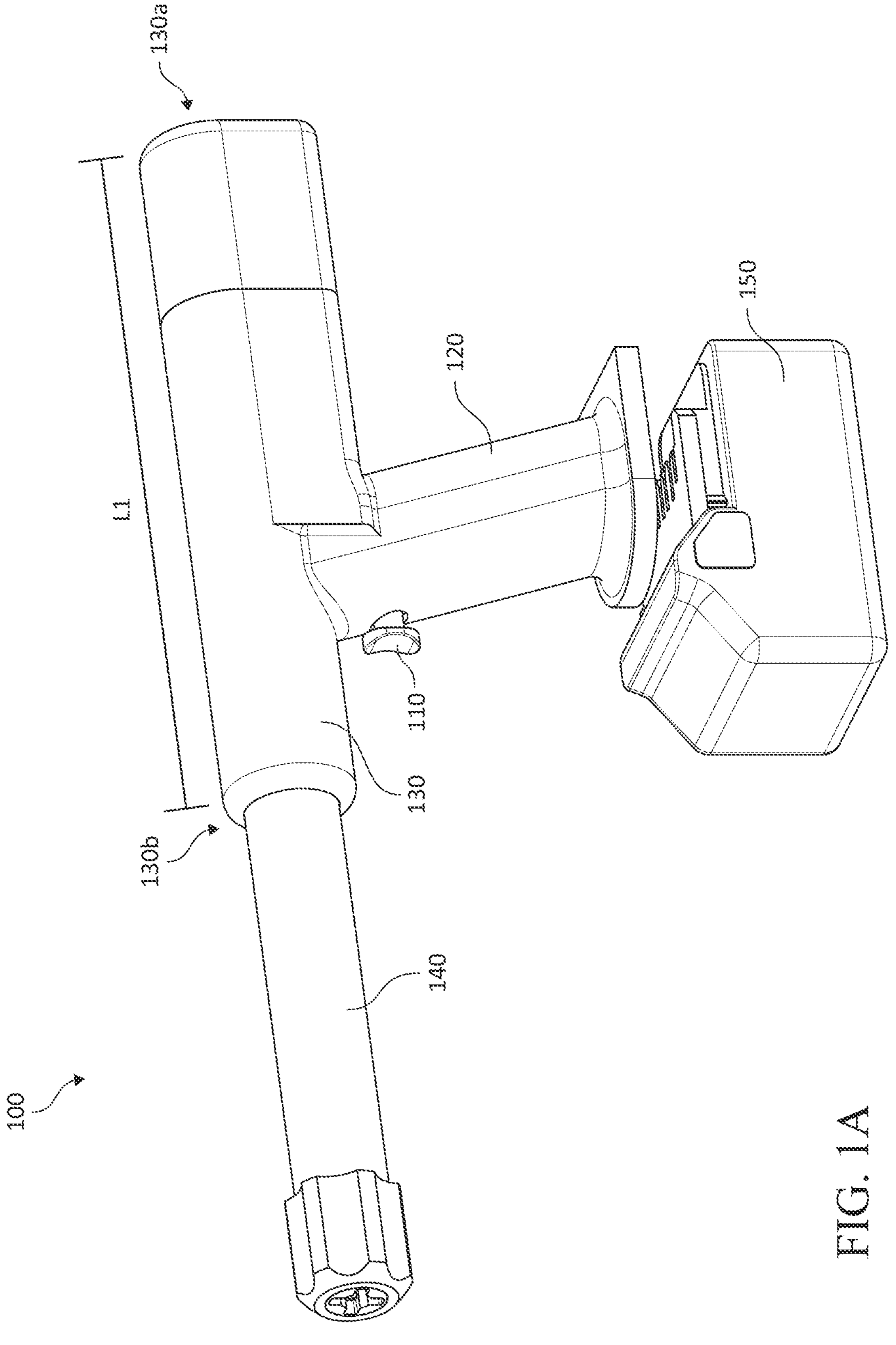
FIGS. 1A and 1B illustrate examples embodiments of an assembly including a surgical impactor.

As shown in FIG. 1A, a surgical impactor can be included as a part of a surgical handpiece. For example, the surgical impactor can be housed within the surgical handpiece 100. The surgical handpiece 100 can include one or more controls for operating and/or adjusting the operational settings of the surgical impactor. In some embodiments, the surgical handpiece can include a user input, such as a button 110. The button 110 can include a trigger. Actuation of the button 110 can control (e.g., begin or stop) operation of the surgical impactor. The surgical handpiece 100 can include a grip 120. The grip 120 can provide the user a place to firmly grasp the surgical handpiece 100, which can lead to better control of the surgical handpiece 100. As illustrated, the grip can comprise a pistol-grip. In some variants, the grip comprises a pencil-grip, rifle-grip, or otherwise. The position of the button 110 relative to the grip 120 can allow users to operate the surgical impactor while grasping the surgical handpiece 100. In some embodiments, the surgical handpiece 100 can be operated using only a single button.

The surgical handpiece 100 can include a barrel 130. The barrel 130 can have a proximal end 130*a* and a distal end 130*b*. The barrel 130 can be attached to the grip 120. In some embodiments, the surgical impactor can be disposed inside a cavity of the barrel 130. The distal end 130*b* of the barrel 130 can receive an implement 140 (e.g., an instrument, implant, etc.). As will be described in more detail below, the surgical impactor can impact the implement 140 which in turn can impact a patient (e.g., a bone), another surgical implement.

The surgical handpiece 100 can include a charging port. The charging port can be positioned, for example, on a bottom surface of the grip 120. The charging port can allow users to attach the surgical handpiece 100 to a power source, such as a battery pack 150. The battery pack 150 can include a port which can receive and secure the charging port of the surgical handpiece 100 to the battery pack 150.

Figure 1B:
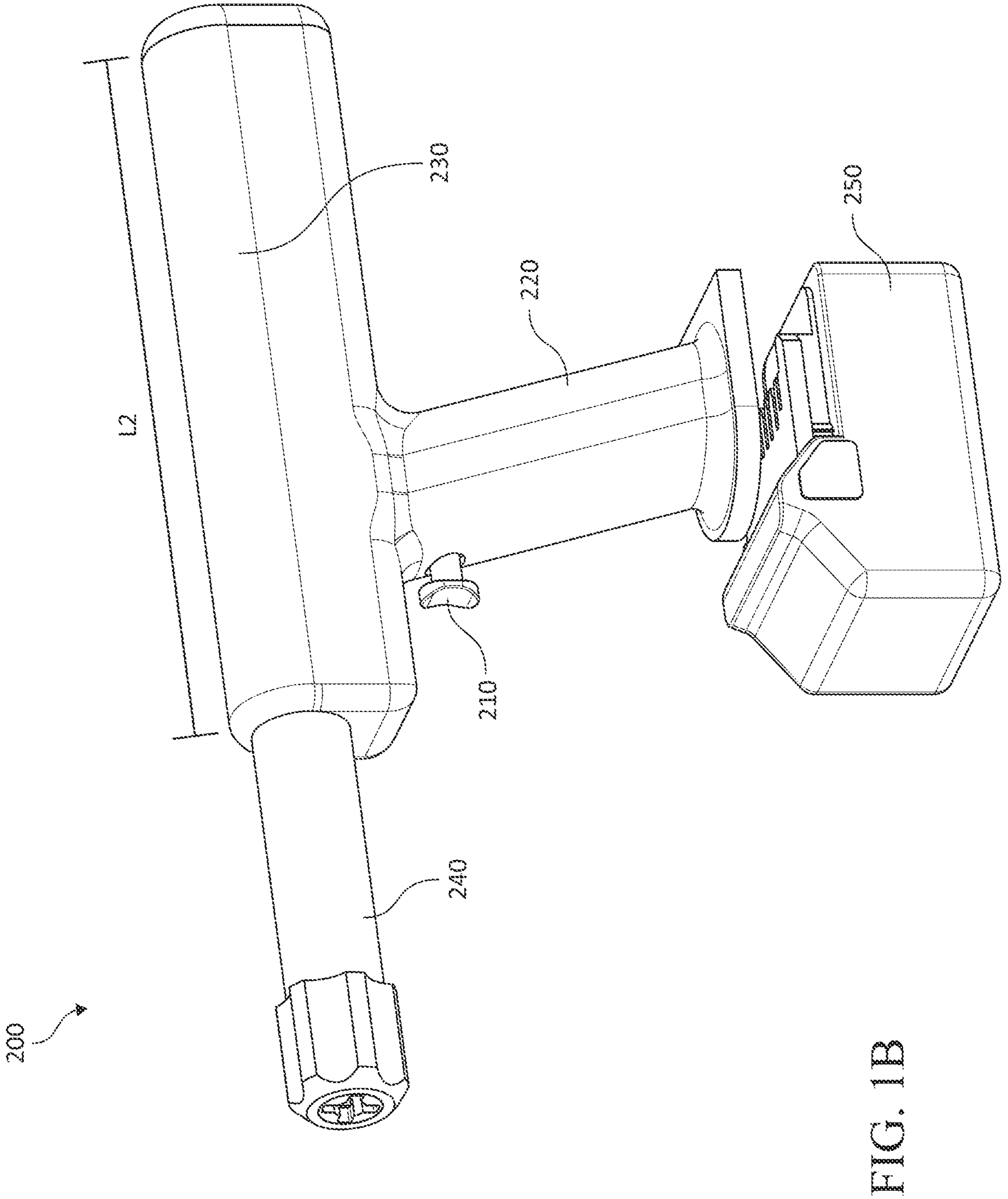

FIG. 1B illustrates another embodiment a surgical handpiece 200. The surgical handpiece 200 shown in FIG. 1B can be similar or identical to the surgical handpiece 100. The surgical handpiece 200 can include a button 210, a grip 220, a barrel 230, an implement 240, and a battery pack 250.

The size and dimensions of the surgical handpiece 100, 200 can vary to accommodate smaller or larger surgical impactors. For example, the surgical handpiece 200 shown in FIG. 1B can include a barrel 230 that is larger (e.g., in length, diameter, etc.) than barrel 130 of the surgical handpiece 100. The larger barrel 230 can accommodate a larger surgical impactor, a larger battery, etc.

In some embodiments, a length of the barrel 130, 230 can vary depending on the surgical procedure and/or patient. For example, a patient's anatomy and/or specific surgical procedure may require a shorter or a longer barrel 130, 230. In some embodiments, the length L1 of barrel 130 can be longer than a length L2 of the barrel 230 of the surgical handpiece 200. Any of the surgical handpieces disclosed herein can include interchangeable attachment points for integration with a navigation system and/or for mounting to a surgical robotic arm.

Figure 2:
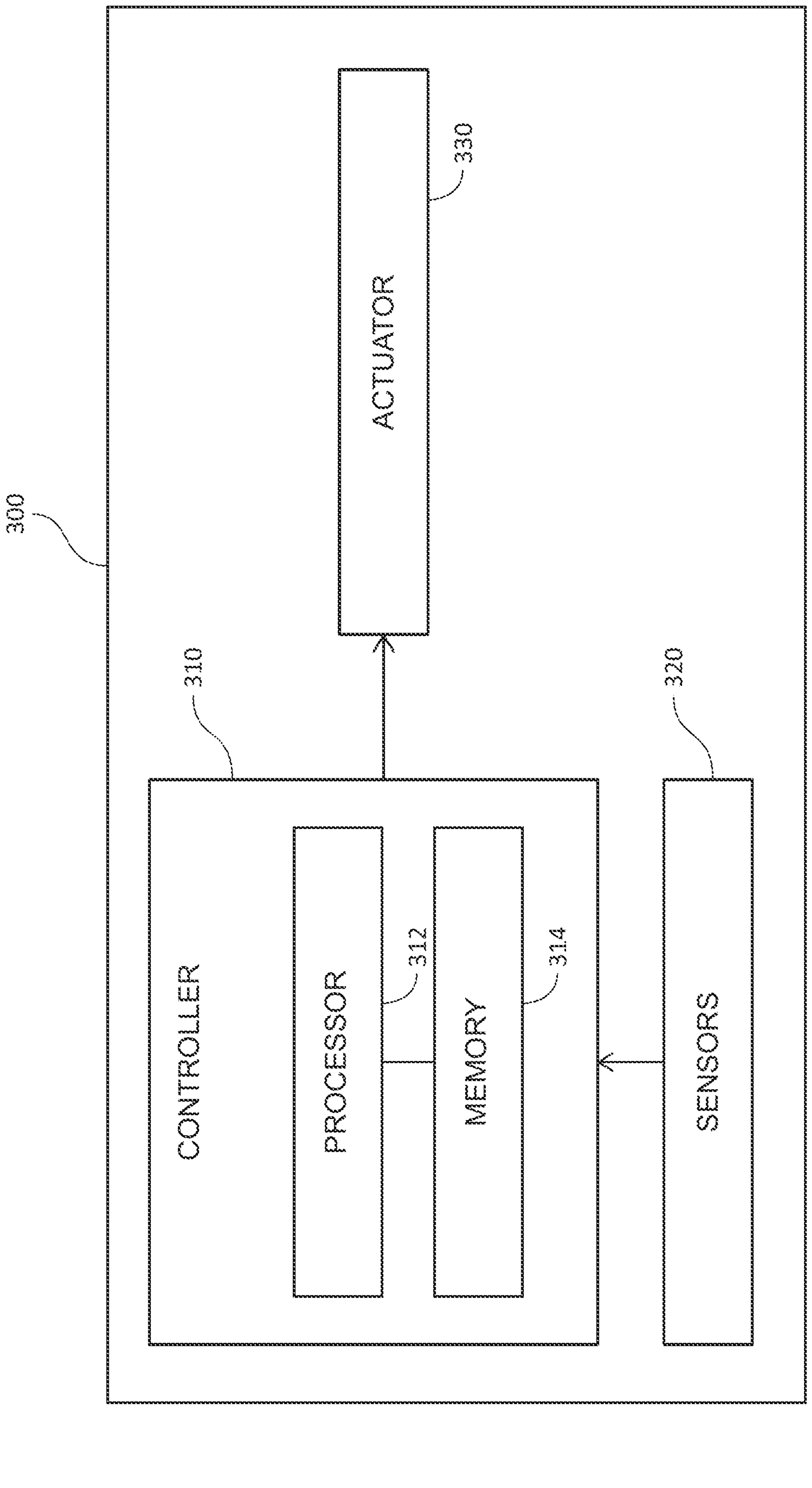
FIG. 2 is a schematic diagram of a controller for a surgical impactor.

FIG. 2 schematically illustrates a surgical impactor 300. The surgical impactor 300 can include a controller 310, one or more sensors 320, and an actuator 330. The controller 310 can include an electronic processor 312 and a memory 314. In some embodiments, the one or more sensors 320 can include at least one of an accelerometer, a force gauge sensor, and a displacement sensor. The one or more sensors 320 can positioned anywhere on the surgical impactor 300. For example, and further described below in relation to FIGS. 3A and 3B, the one or more sensors 320 can be positioned along an implement of the surgical impactor 300. The one or more sensors 320 can detect, collect, and/or signal data relating to, for example, the operation of the surgical impactor 300. The data collected by the one or more sensors 320 can be transmitted to the controller 310 of the surgical impactor 300. The data from the one or more sensors 320 can be received by the controller 310 can be processed by the processor 312 of the controller 310. The controller 310 can use the data from the one or more sensors 320 to generate data relating to, for example, the acceleration of the implement, the amount of force applied to the implement, and/or the displacement/frequency of the implement 460 and/or the hammer head relative to a housing or hammer housing of the surgical impactor 300. The data generated by the processor 312 can stored on the memory 314 and/or can be used to adjust, for example, operation of the actuator 330 driving the frequency, direction, and force of a rod of the surgical impactor 300.

Figure 3A:
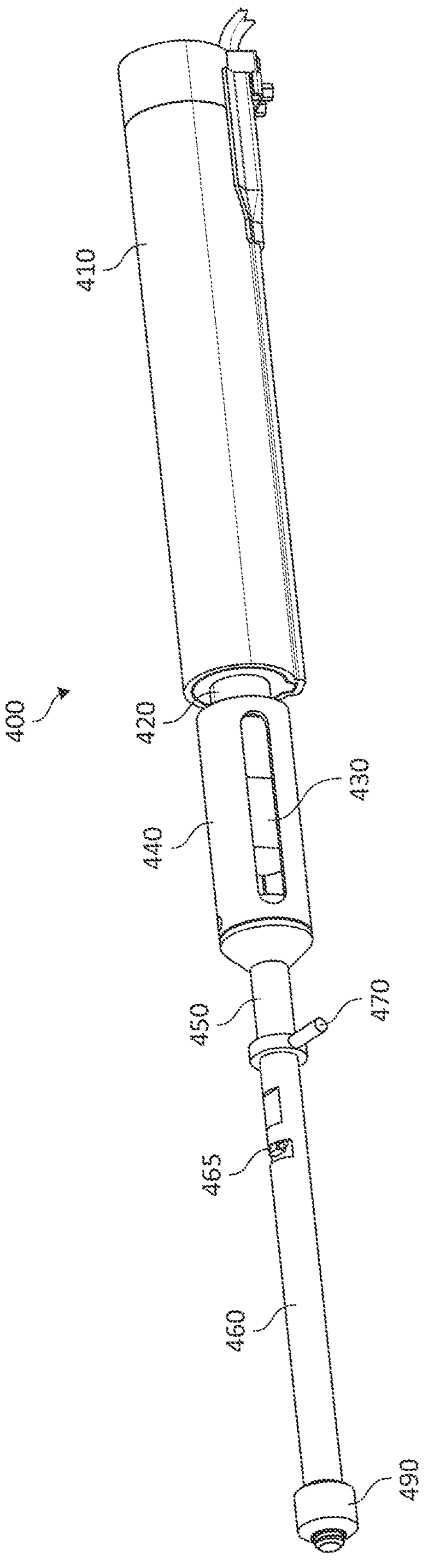
FIG. 3A illustrates another example embodiment of a surgical impactor.
Figure 3B:
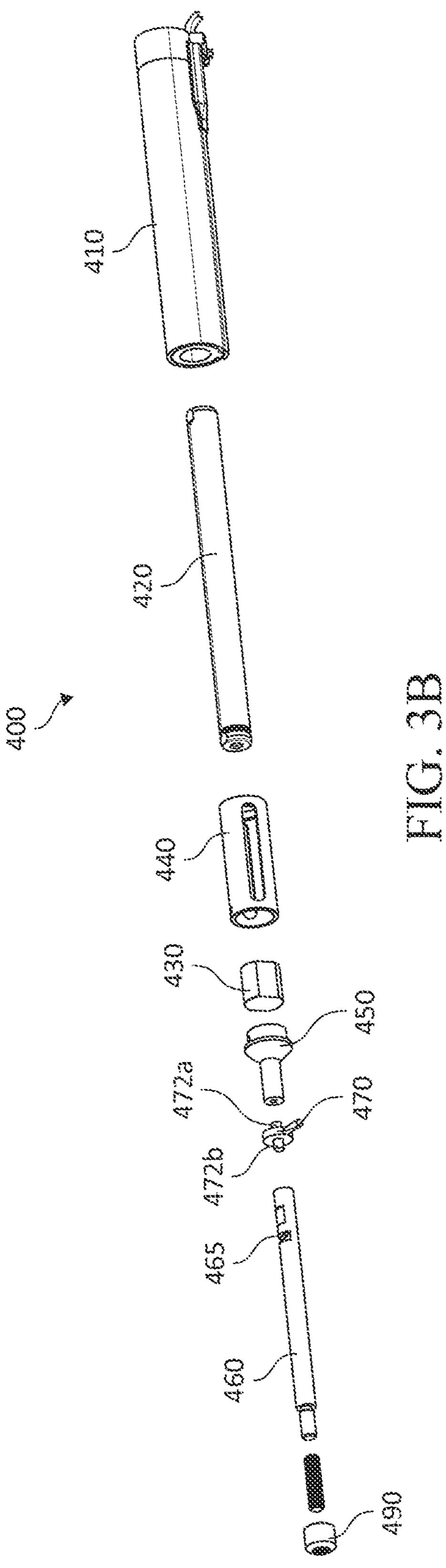
FIG. 3B illustrates an exploded view of the surgical impactor of FIG. 3A.

FIGS. 3A and 3B illustrate another example of a surgical impactor 400. The surgical impactor 400 can include a housing 410, a rod 420, a hammer head 430, and a hammer housing 440. In some implementations, the surgical impactor 400 can include an adapter 450 and/or an implement 460. The housing 410, rod 420, hammer head 430, hammer housing 440, adapter 450, and implement 460, as well as the overall surgical impactor 400, are discussed in more detail below.

Implement

Figure 4A:
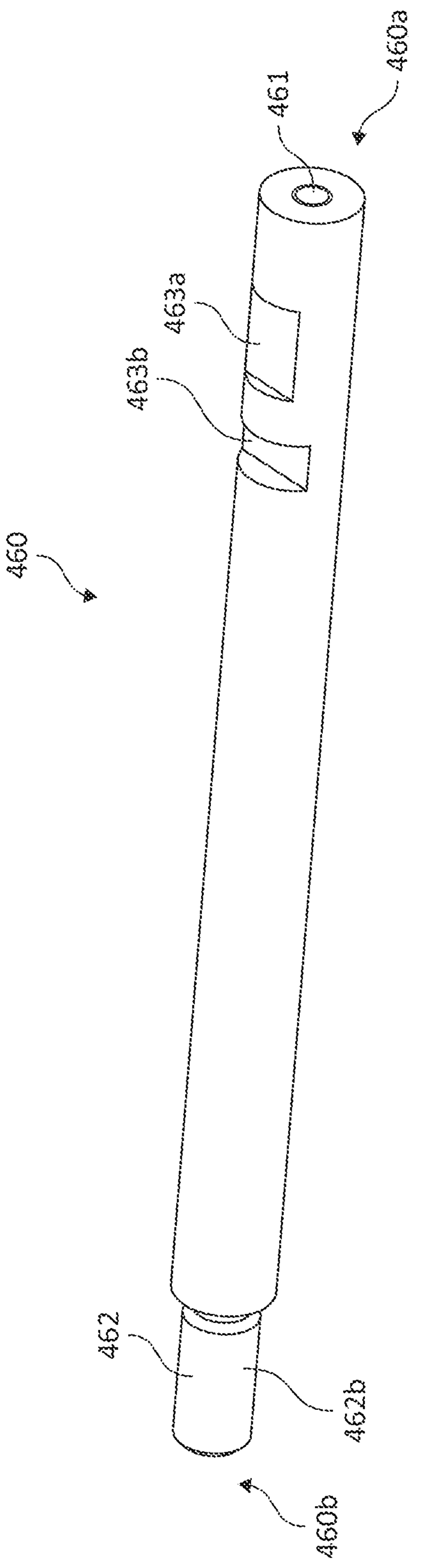
FIGS. 4A and 4B illustrate an implement of the surgical impactor of FIG. 3A.
Figure 4B:
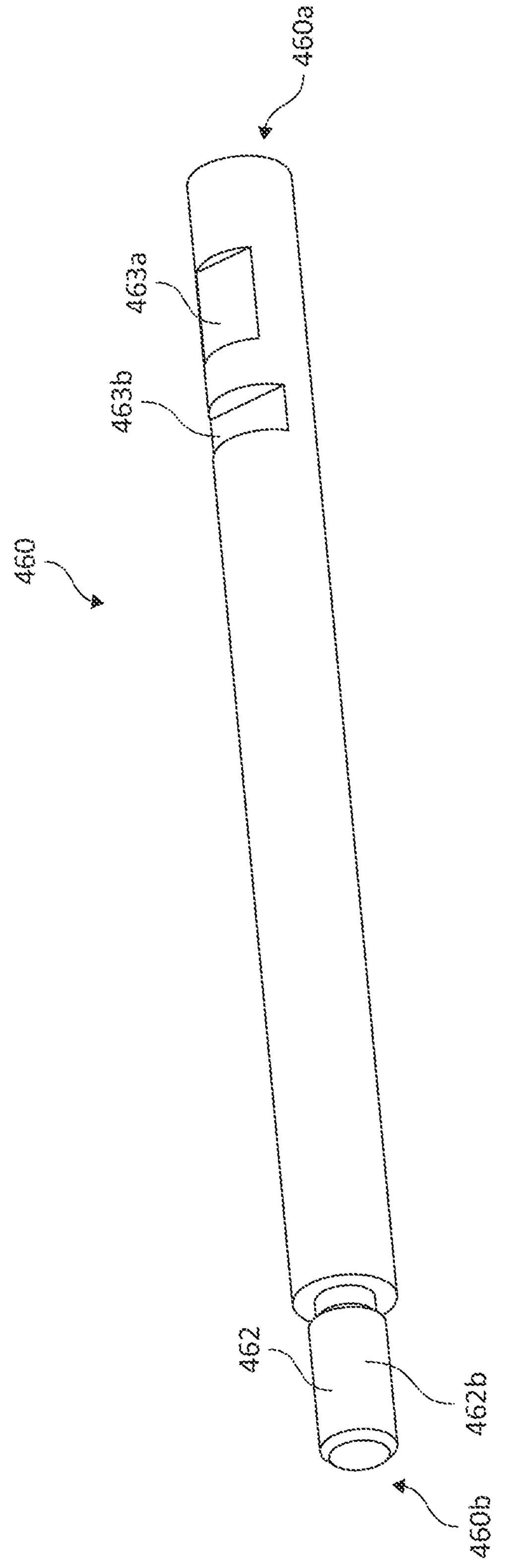

FIGS. 4A and 4B illustrate the implement 460. In some implementations, the implement is configured to convey impact force from the surgical impactor 400 to a surgical implant, such as the ball of an artificial hip. In certain variants, the implant is configured to convey impact force from the surgical impactor 400 to a surgical tool, such as a coupling configured to connect to an implant. In some embodiments, the implant is configured to apply impact force to a securement device, for example, nails, staples, or otherwise. As will be described in more detail below, the axial motion of the hammer head inside the hammer housing 410 can cause the implement 460 to move along an axial direction.

The implement 460 can include a proximal end 460*a* and a distal end 460*b*. The distal end 460*b* can include a tip 462. In some embodiments, a cavity 461 can be disposed on the proximal end 460*a*. The proximal end 460*a* of the implement 460 can be connected to the adapter 450. The implement 460 be mechanically connected (e.g., directly) to the adaptor 450 and/or to the hammer housing 440. In some embodiments, the implement 460 is connected to the adapter 450 via a connector 470 (See FIG. 3B). In some variants, the connector 470 comprises a load cell. In some embodiments, the connector 470 comprises a rod, such as a threaded rod. The connector 470 can include a first connecting member 472*a* and a second connecting member 472*b*. The first connecting member 472*a* can be received and secured by (e.g., threadably connected to) a recess 451 of the adapter 450 and the second connecting member 472*b* can be received and secured by (e.g., threadably connected to) the cavity 461. The connector 470 can be configured to secure the adapter 450 and the implement 460 to each other. Other surgical instruments can be attached to the adapter 450.

The implement 460 can include one or more recesses along the length of the implement 460. For example, the implement 460 can include a first recess 463*a* and a second recess 463*b*. Although reference is made to the implement 460 including two recesses, the implement 460 can include less than or more than two recesses (e.g., one, three, four five, etc.). The first and second recesses 463*a*, 463*b* can beneficially receive and secure additional surgical instruments and/or sensors. For example, as shown in FIG. 3A, a sensor 465 can be secured to the second recess 463*b*. As illustrated, the one or more recesses can comprise a flat section. The flat section can facilitate securement and/or maintain the circumferential position of the surgical instruments and/or sensors relative to the implement 460.

The sensor 465 can include, for example, an accelerometer, a force gauge sensor, and/or a displacement sensor. The data sensed by the sensor 465 can be transmitted to a controller of the surgical impactor 400 (e.g., controller 310). The data received by the controller can be processed by a processor of the controller to generate data relating to, for example, the acceleration of the implement 460, the amount of force applied to the implement 460, and/or the displacement of the implement 460 and/or the hammer head 430 relative to the housing 410. The data generated by the processor can be used to adjust, for example, operation of the actuator driving the frequency, direction, and force of the rod 420. In certain implementations, the surgical impactor 400 can include a sensor configured to identify characteristics of the implement 460, the implant, or otherwise. For example, in some embodiments, the sensor can detect a type, intended use, weight, mass, and/or other characteristics. The controller can use such information in controlling the linear actuator, such as in determining the amount of power to use in driving the rod 420 and/or creating the impact force.

Electronic identification of the implement 460 and/or its characteristics can allow for different default electronically controlled impact settings, such as based on the size, shape, or other characteristics that affect optimal impact energy and frequency. The implement 460 may be electronically identified with a sensor, for example a hall effect sensor, which can be positioned within the handpiece (e.g., handpieces 100, 200, and/or the surgical impactor 400) at the implement attachment point (e.g., where the implement 460 attaches to the adapter 450 via the connector 470). The hall effect sensor can detect the presence of and/or magnetic field strength of one or more magnets embedded within the shaft of the implement 460 positioned at variable distances from the hall effect sensor.

The displacement of the implement 460 after impact may be estimated using data from the from one or more accelerometers. In some implementations, the displacement of the implement 460 after impact may be estimated by, for example, double integrating acceleration data from one or more accelerometers with respect to time. If the sensor detects excessive displacement of the implement 460 after impact, the controller (e.g., with software executed thereon) can infer or determine the presence of softer bone or other tissue and adjust the operation of the impactor accordingly. For example, in response to detecting excessive displacement of the implement 460, the controller can reduce the electric current that drives magnetic acceleration of the rod 420 and/or hammer head 430. This can reduce impact energy and the rate of displacement of the implement 460, which can provide the surgeon or other user with more precise control of the displacement and or positioning of the implement 460 (and/or implant) and/or reduce the risk of excessive impact or misdirected impact.

In some embodiments, the tip 462 of the implement 460 can receive and secure additional surgical devices. The tip 462 can include a thread 462*a* which can beneficially secure the implement 460 to additional surgical devices. For example, an impactor tip 490 can be attached to the tip 462 (see FIG. 3A). The impactor tip 490 can include an opening 492 and a threaded surface along the opening 492 to facilitate attachment of the impactor tip 490 to the thread 462*a* of the tip 462. An accelerometer embedded in the housing 410 can monitor recoil and vibration experienced by the user. If the magnetic recoil forces applied to the housing 410 exceed the opposing force applied by the user, recoil acceleration occurs that is proportional to the force imbalance. An accelerometer in the housing 410 can monitor and limit acceleration of the handpiece if the acceleration exceeds a pre-defined threshold by automatically reducing the magnetic recoil forces until acceleration is at or below the pre-defined threshold. This can beneficially reduce the impact energy delivered to the implement 460 until the user applies sufficient force in the direction of impact.

Adapter

Figure 5A:
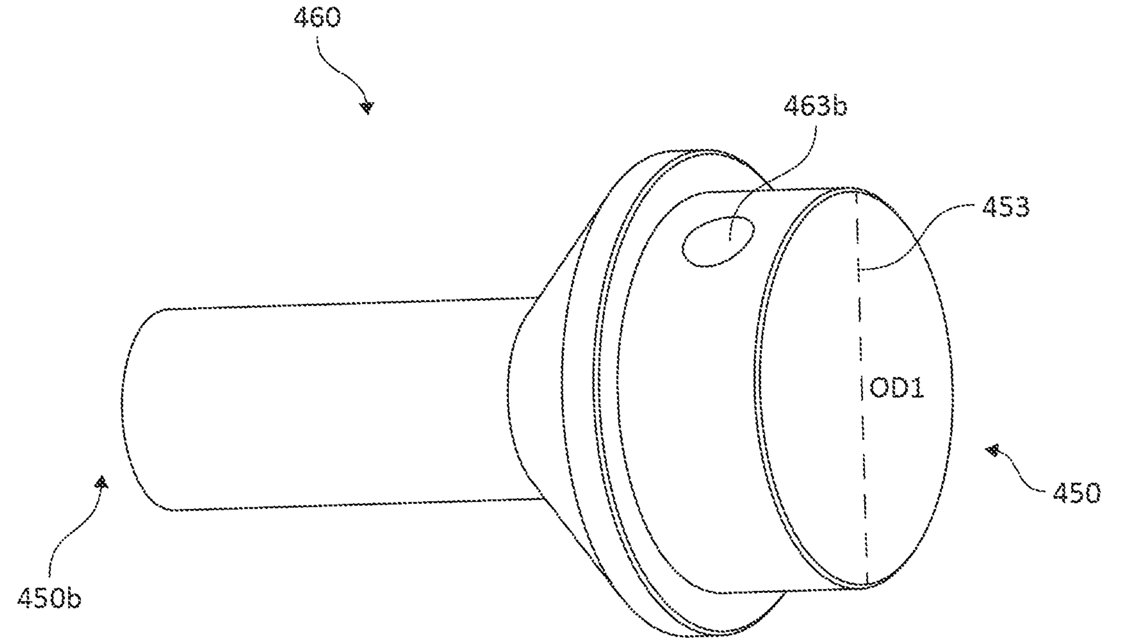
FIGS. 5A and 5B illustrate an adapter of the surgical impactor of FIG. 3A.
Figure 5B:
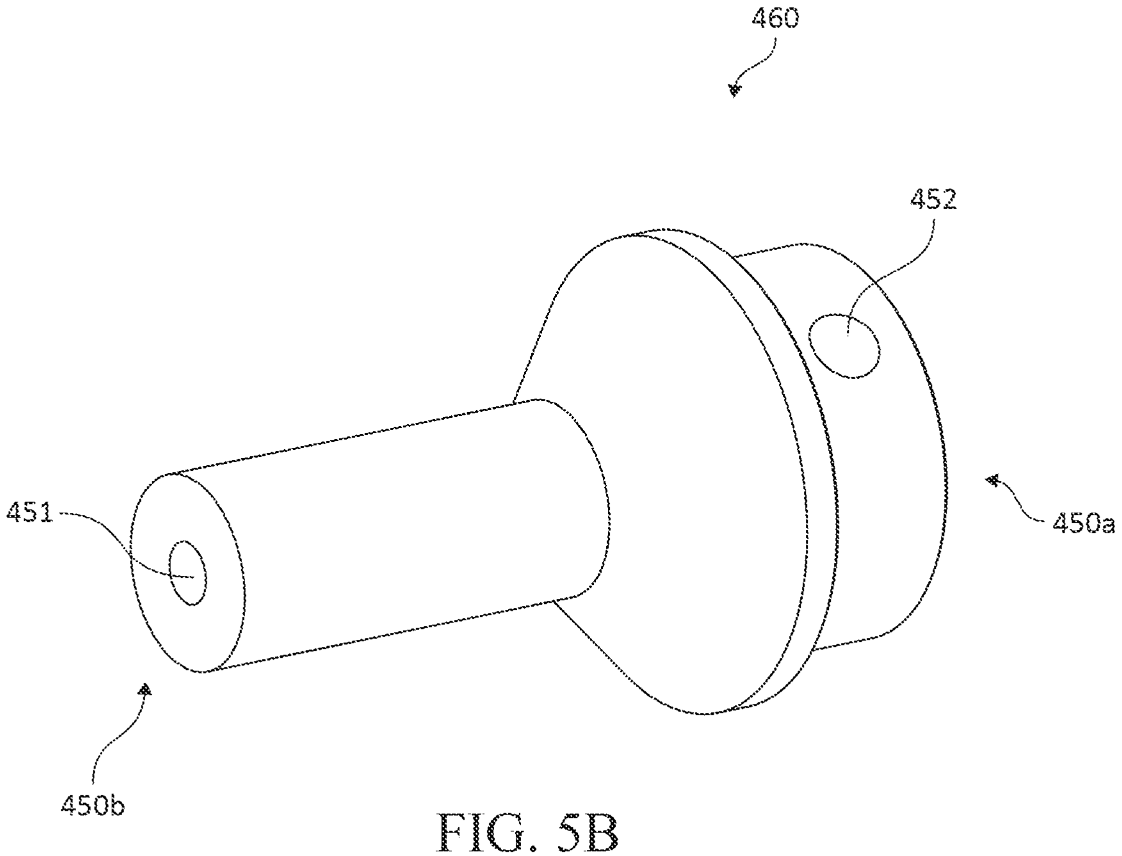

As illustrated in FIGS. 5A and 5B, the adapter 450 can include a proximal end 450*a* and a distal end 450*b*. The distal end 450*b* can include the recess 451. The recess 451 can receive and secure the first connecting member 472*a* of the connector 470. The proximal end 450*a* can include an opening 452. The adapter 450 can be secured to the hammer housing 440 by inserting the proximal end 450*a* of the adapter 450*a* into a distal aperture 441*b* of the hammer housing 440. An outer diameter OD1 of the proximal end 450*a* can be substantially equal to or less than an internal diameter ID1 of the hammer housing 440. This can beneficially allow the proximal end 450*a* to fit inside the distal aperture 441*b* of the hammer housing 440. In some embodiments, the proximal end 450*a* can include a flat surface 453. The adapter 450 can have an intermediate portion that connects the proximal and distal ends 450*a*, 450*b*. As illustrated, the intermediate portion can be conical or otherwise.

Because the hammer housing 440 and/or the adapter 450 can be subject to direct impacts by the hammer head 430, it may be desirable to inhibit or prevent the adapter 450 from detaching from the hammer housing and vice versa. One or more screws or other securement devices can be used to securely and/or rigidly connect the adapter 450 to the hammer housing 440. The opening 452 of the adapter 450 can be aligned with holes 444 of the hammer housing 440 when the adapter 450 is secured to the hammer housing 440. One or more screws can be inserted on the opening 452 and the holes 444 to inhibit or prevent the adapter 450 from sliding off the hammer housing 440.

The adapter 450 can include an edge 454. The edge 454 can extend outwardly from the proximal end 450*a* of the adapter 450. The edge 454 can inhibit or prevent the adapter 450 from extending into the hammer housing 440 beyond the edge 454. The edge 454 can interface (e.g., abut) with a corresponding distal edge of the housing 440. This can provide a physical interference in the axial direction, which can facilitate transferring force between the housing 440 and the adapter 450.

Hammer Housing

Figure 6A:
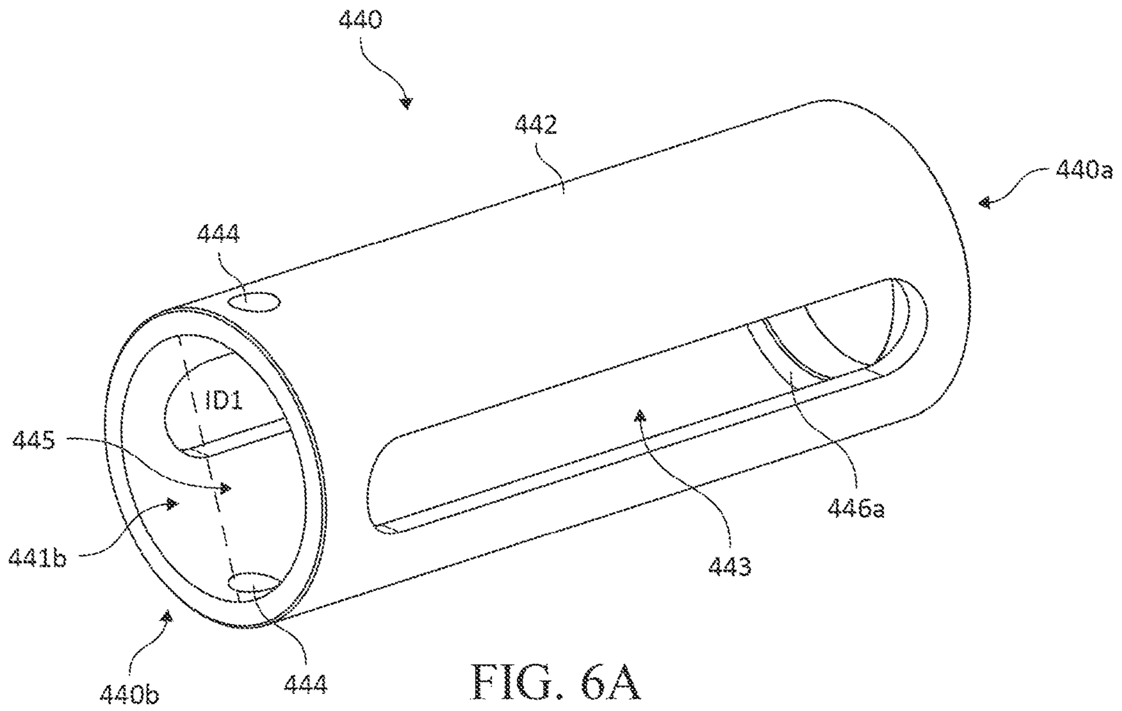
FIGS. 6A and 6B illustrate a hammer housing of the surgical impactor of FIG. 3A.
Figure 6B:
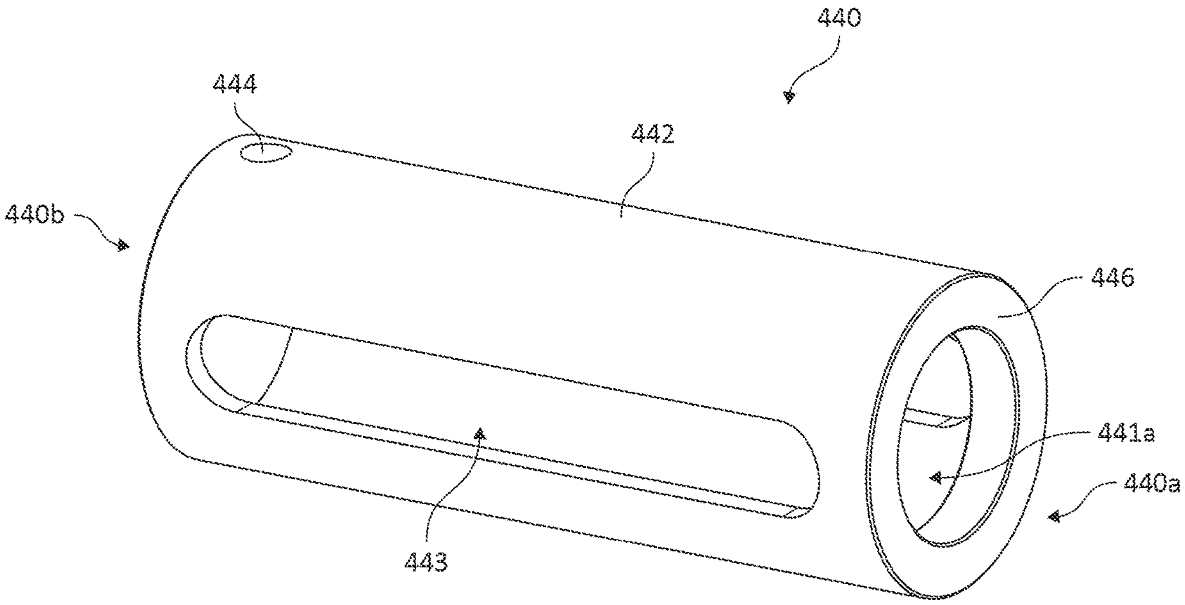

FIGS. 6A and 6B, illustrate the hammer housing 440. The hammer housing 440 can receive the hammer head 430, as discussed in more detail below. The hammer housing 440 can include a proximal end 440*a*, a distal end 440*b*, a body 442, and a cavity 445 inside the body 442. In certain variants, the hammer housing can provide a buffer or damper and/or can enable the adapter 450 and implement 460 to be at least partially independent of the hammer head 430 and rod 420. For example, in certain situations, the hammer head 430 and rod 420 can move proximally or distally a distance without causing matching movement of the adapter 450 and implement 460.

The body 442 can include one or more windows 443. For example, as illustrated, the hammer housing 440 can comprise two windows on approximately opposite sides of the hammer housing 440. The windows 443 can allow the user to visually inspect the interior of the hammer housing 440, such as to see movement of the hammer head 430 during operation of the surgical impactor 400. In some embodiments, the window 443 can serve as a guide and/or track for the hammer head 430 inside the hammer housing 440. For example, a protrusion on the hammer head 430 can be received in the window 443. The window 443 can be configured to, for example, allow the hammer head 430 to move axially relative to the hammer housing 440, inhibit or prevent circumferential movement of the hammer head 430 relative to the hammer housing 440, and/or restrict the hammer head 430 to only one degree of freedom of movement relative to the hammer housing 440.

A proximal aperture 441*a* can be positioned on the proximal end 440*a*. A distal aperture 441*b* can be positioned on the distal end 440*b*. In some embodiments, the hammer housing can include an edge 446 positioned on the proximal end 440*a* which can make the proximal aperture 441*a* smaller than the distal aperture 441*b*. The edge 446 on the proximal aperture 441*a* can inhibit or prevent the hammer head 430 from escaping the hammer housing 440 via the proximal end 440*b* but allow the rod 420 to extend through the proximal aperture 441*a*.

The hammer housing 440 can include one or more holes 444. The holes 444 can be positioned on one end of the hammer housing 440, for example distal end 440*b*. As previously described, one or more screws or other securement devices can extend through the opening 452 of the adapter 450 and the holes 444 of the hammer housing 440 to secure the adapter 450 to the hammer housing 440.

Hammer Head

Figure 7A:
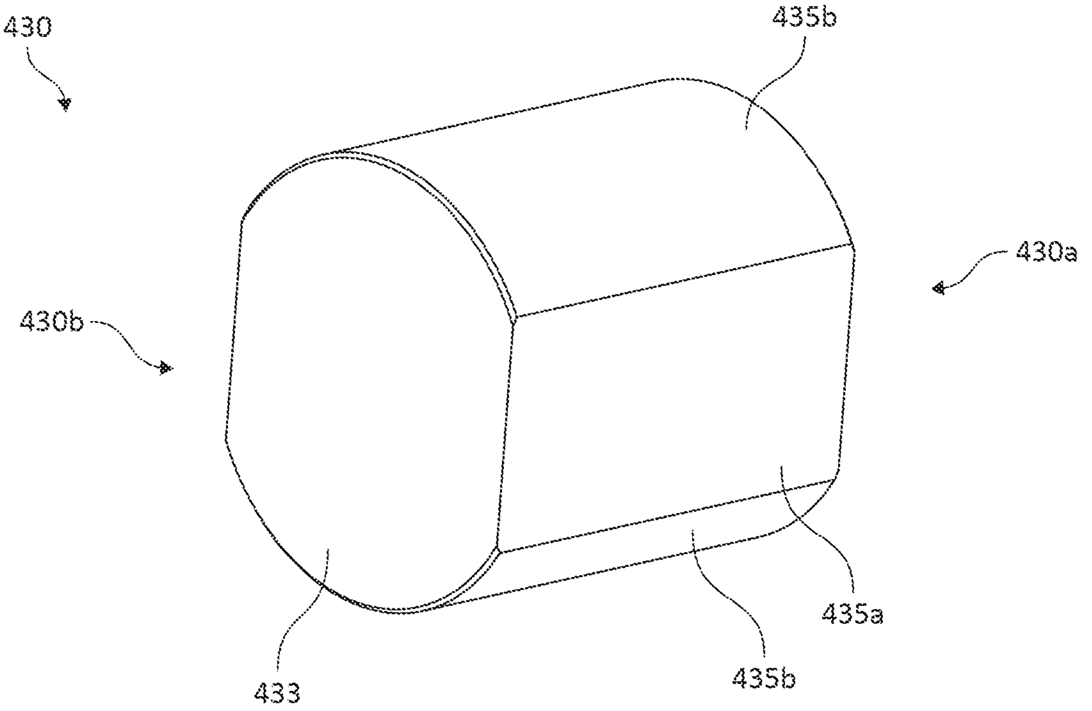
FIGS. 7A and 7B illustrate a hammer head of the surgical impactor of FIG. 3A.
Figure 7B:
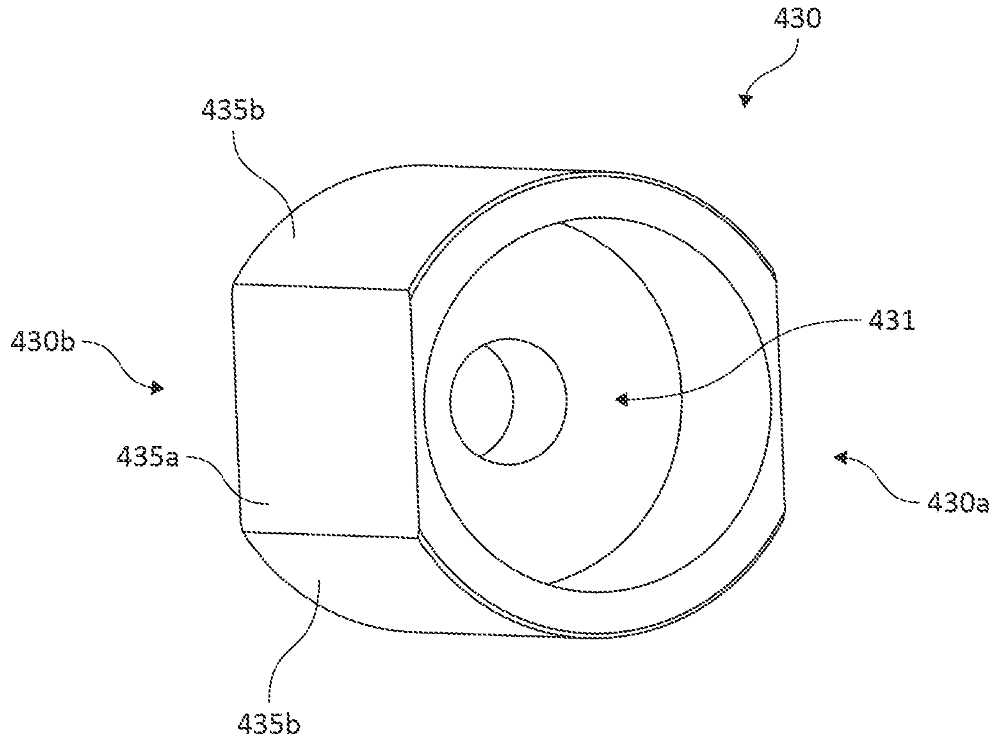

FIGS. 7A and 7B illustrate the hammer head 430. In various embodiments, the hammer head 430 is connected to the rod 420 and is received in and/or able to move axially relative to the hammer housing 440. In several embodiments, the hammer head "floats" within the hammer housing. For example, the hammer head 430 can move within and relative to the hammer housing 440. In some embodiments, the hammer head 430 can recoil within the hammer housing 440. The linear travel of the hammer head 430 can be limited by a length of the hammer housing 440. In certain implementations, the hammer head 430 is removably connected to the rod 420, such as with a threaded connection.

The hammer head 430 can include a proximal end 430*a* and a distal end 430*b*. In some embodiments, the hammer head 430 includes a recess 431, such as along the proximal end 430*a*. The recess 431 can include a shape corresponding to the shape of a distal end 420*b* of the rod 420. This can beneficially allow the recess 431 to receive and secure the distal end 420*b* of the rod 420. In some embodiments, the edge 420 can include a threaded surface (not shown). The threaded surface of the recess 420 can beneficially receive and secure a thread 421 of the rod 420.

The distal end 430*b* of the hammer head 430 can include a flat surface 433. The flat surfaces 433, 453 of the hammer head 430 and the adapter 450 can beneficially allow the force generated by the impact of the hammer head 430 with the adapter 450 to be distributed over the entire or substantially the entire distal end 450*a* of the adapter 450.

In some embodiments, as illustrated, the hammer head 430 can include one or more (e.g., two) flat edges 435*a* and a two curved edges 435*b* extending from the flat edges 435*a*. In some variants, an outer shape of the hammer head 430 substantially corresponds to an inner shape of the hammer housing 440 and/or the cavity 445.

A height H1 of the hammer head 430 can be substantially equal to or less than the internal diameter ID1 of the hammer housing 440. This can beneficially allow the hammer head 430 to fit and slide inside cavity 445 of the hammer housing 440. In some embodiments, the hammer head 430 can be inserted into the cavity 445 of the hammer housing 440 via the distal aperture 441*b* of the hammer housing 440. Inside the hammer housing 440, the hammer head 430 can be inhibited or prevented from escaping the cavity 445 of the hammer housing 440 when the adapter 450 is attached to the hammer housing 440. That is, the edge 446 can inhibit or prevent the hammer head 430 from escaping the hammer housing 440 via the proximal end 440*a*, and the proximal end 450*a* of the adapter 450 can inhibit or prevent the hammer head 430 from escaping the hammer housing 440 via the distal end 440*b*.

Rod

Figure 8A:
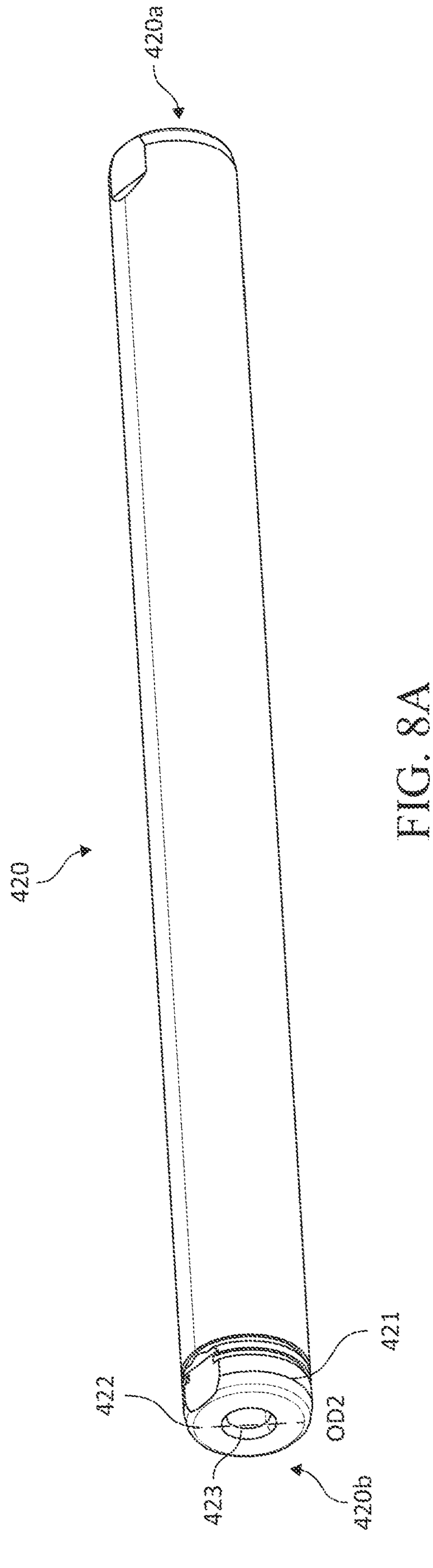
FIGS. 8A and 8B illustrate a rod of the surgical impactor of FIG. 3A.
Figure 8B:
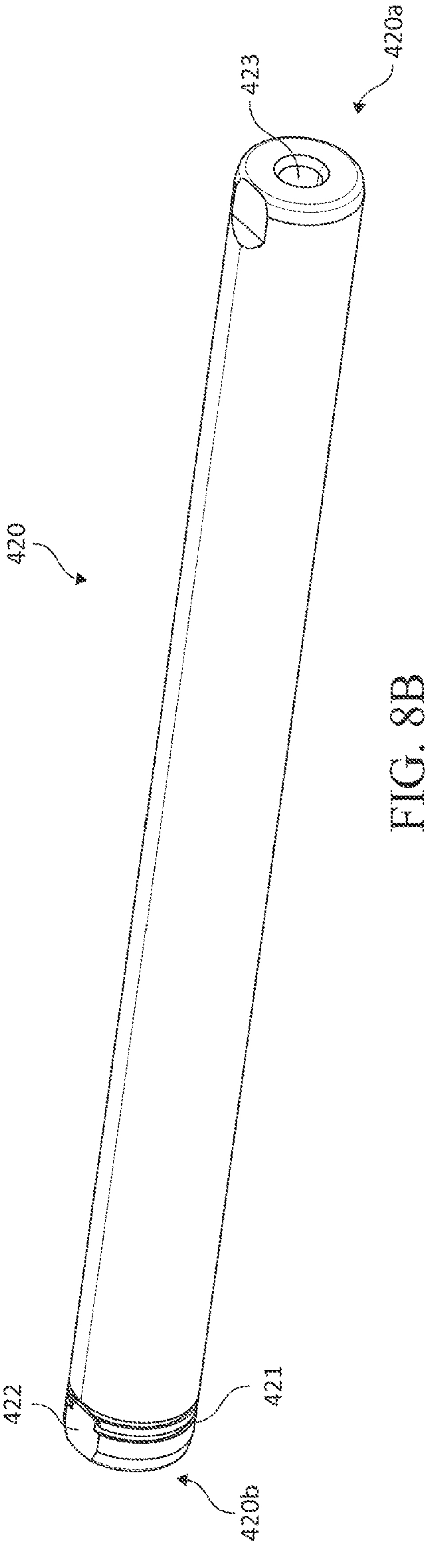

As shown in FIGS. 8A and 8B, the rod 420 can include a proximal end 420*a* and a distal end 420*b*. In some embodiments, the rod 420 has a connector (e.g., thread 421) along surface of a distal tip 422. The thread 421 of the distal thread 421 can facilitate attachment of the rod 420 to the hammer head 430. For example, the recess 431 of the hammer head 430 receive and secure the distal tip 422 of the rod 420. In some embodiments, the recess 431 of the hammer head 430 can include a threaded surface which can interact with the thread 421 of the distal tip 422 to secure the rod 420 to the hammer head 430.

The rod 420 can include an opening 423 extending axially along, partially or completely, the rod 420. In some embodiments, the rod 420 can include a tubular shape. The rod 420 can include a shape other than a tubular shape. The rod 420 can include an outer diameter OD2 smaller than an inner diameter ID2 of a lumen 415 of the housing 410. This can beneficially allow the rod 420 to fit inside the cavity 415 of the housing 410. In some embodiments, the rod 420 can be dynamically sealed inside housing 410 using, for example, gaskets, seals, etc.

Housing

Figure 9A:
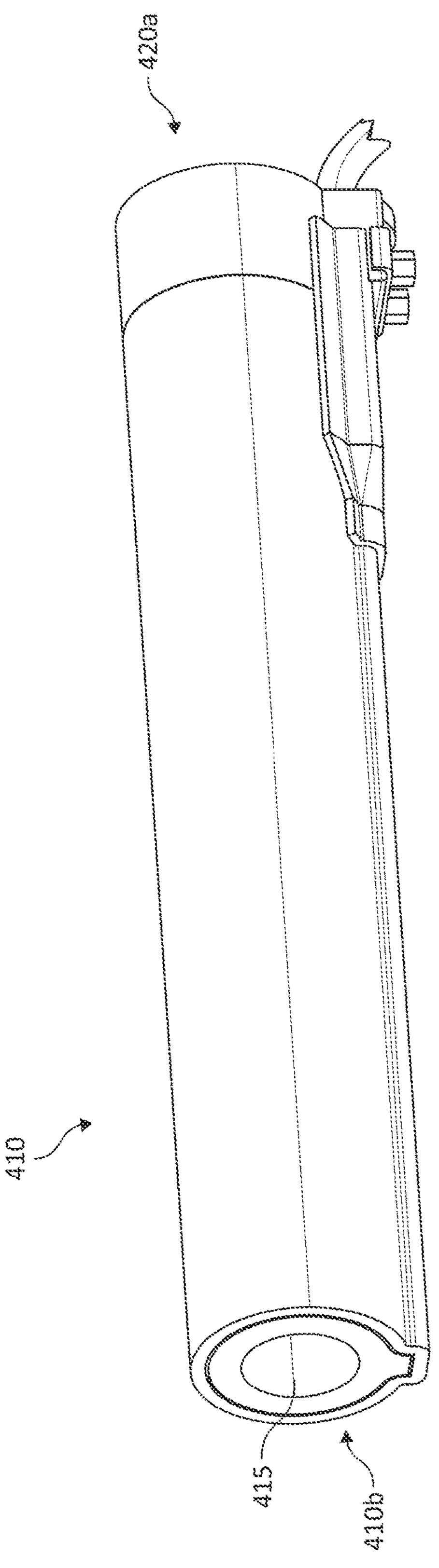
FIGS. 9A and 9B illustrate a housing of the surgical impactor of FIG. 3A.
Figure 9B:
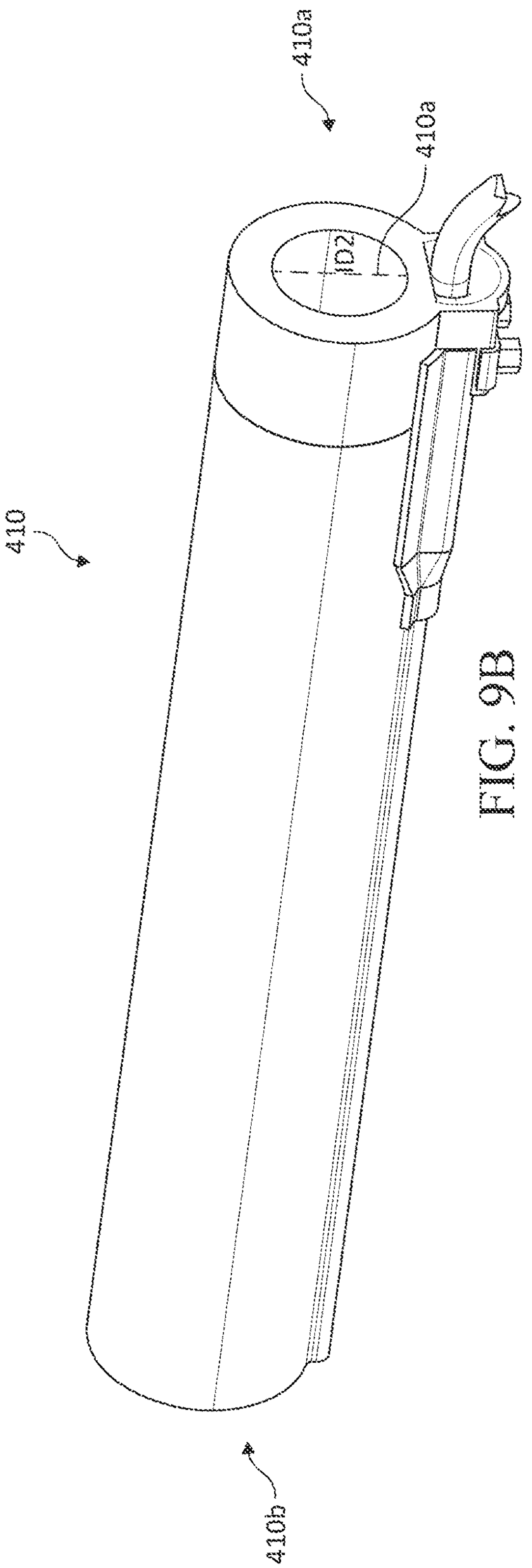

FIGS. 9A and 9B illustrate the housing 410. The housing 410 can include a proximal end 410*a*, a distal end 410*b*, and a lumen 415 (also called a cavity or cannula). The lumen 415 can receive the rod 420. The lumen 415 can be sealed, such as being air and/or liquid tight other than at proximal and distal openings, as illustrated. The housing 410 can include a linear actuator that causes movement of the rod 420 relative to the housing 410, as described in more detail below.

The lumen 415 can extend axially along the housing 410, such as completely from the proximal end 410*a* to the distal end 410*b*. The lumen 415 can provide a through-hole and/or a continuous passage through the housing 410. The lumen 415 can enable the rod 420 to be inserted and/or removed from the housing 410 via each of the proximal end 410*a* and the distal end 410*b*. The lumen 415 can facilitate cleaning and/or use of the surgical impactor 400.

In some embodiments, a source of power can be positioned along the proximal end 410*a* of the housing 410. For example, a battery pack for powering the surgical impactor 400 can be mounted to an exterior surface of the housing 410 along or adjacent the proximal end 410*a*. In some variants, the source of power comprises a wired connection to an off-board power supply, such as an electrical outlet.

As mentioned above, the housing can receive the rod 420. In some embodiments, the entire rod 420 can be disposed inside the lumen 415 of the housing 410. In some embodiments, however, only a portion of the rod 420 is disposed inside the lumen 415. The rod 420 can move along the lumen 415 in an axial direction. For example, the rod 420 can move along an axis A1 in a proximal to distal direction and/or a distal to proximal direction. In several embodiments, the rod 420 can be removed from the lumen 415 of the housing 410, such as through the proximal and/or distal openings of the lumen 415. The ability to remove the rod 420 from the lumen 415 of the housing 410 beneficially allows users to remove the rod 420 for servicing (e.g., cleaning, lubrication, sterilization, etc.).

Operation of the Impactor

Figure 10A:
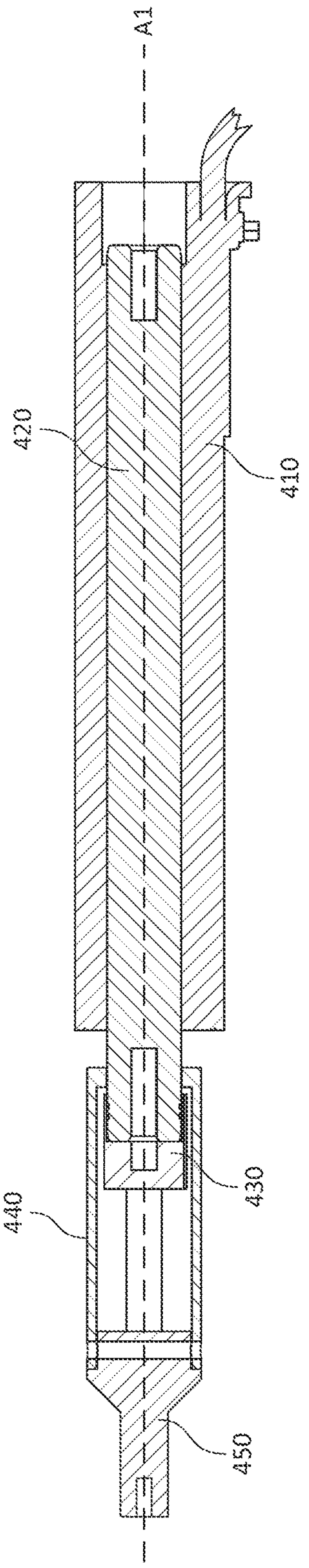
FIGS. 10A-10C illustrate cross-sectional views of the surgical impactor of FIG. 3A in various operational states, with the hammer extending through a lumen of the housing and the hammer head moving axially along the hammer housing.
Figure 10B:
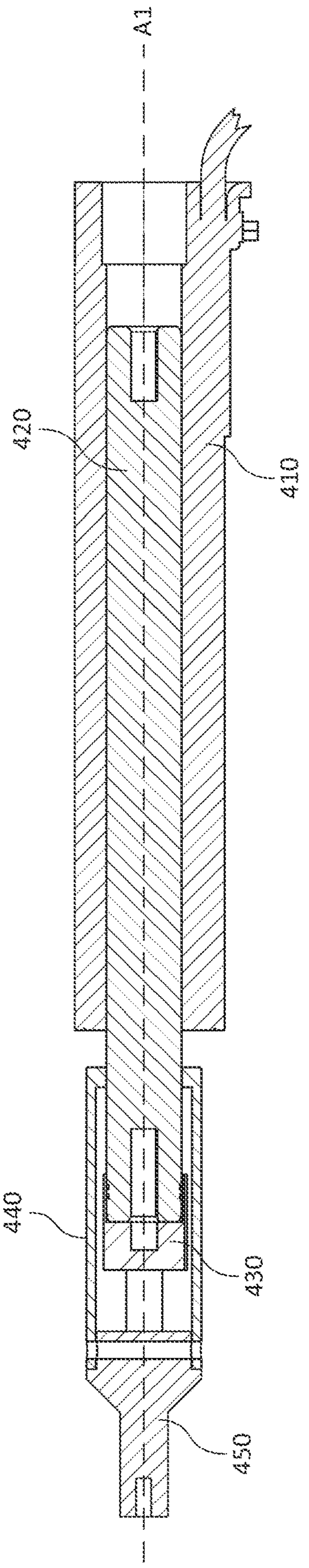
Figure 10C:
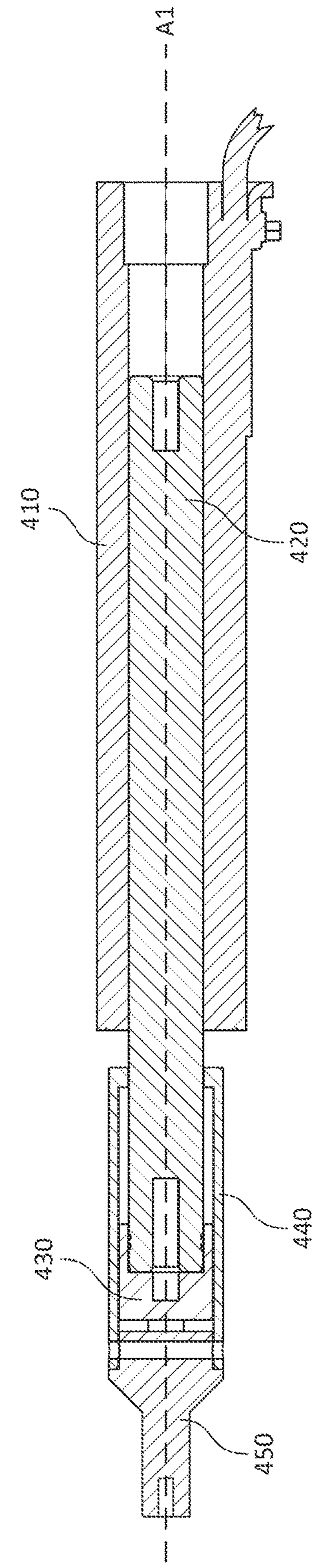

FIGS. 10A-10C illustrate the surgical impactor in various stages of operation. As described above, the rod 420 can move along an axis A1 along an axial direction (e.g., in a proximal to distal direction and/or a distal to proximal direction). The movement of the rod 420 along the axis A1 can cause the hammer head 430 to move along the axis A1 inside the hammer housing 440 when the hammer head 430 is attached to the rod 420. FIGS. 10A-10C illustrate the movement of the hammer head 430 inside the hammer housing 440.

The surgical device can be configured such that the housing 410 moves the rod 420 which in turn moves the hammer head 430. The hammer head 430 can move inside the hammer housing 440 from a proximal to distal direction along the axis A1. In several implementations, the hammer head 430 can move, for example, from a proximal position in which the proximal end 430*a* of the hammer head 430 is adjacent or in contact with an interior portion 446*a* of the edge 446, as shown in FIG. 10A, to an intermediate position in which the hammer head 430 is between and axially spaced apart from the interior portion 446*a* of the edge 446 and the proximal end 450*a* of the adapter 450, as shown in FIG. 10B, to a distal position in which the distal end 430 of the hammer head 430 is adjacent or in contact with the proximal end 450*a* of the adapter 450, as shown in FIG. 10C.

In several implementations, the hammer head 430 can move inside the hammer housing 440 from a distal to proximal direction along the axis A1. That is, the hammer head 430 can move, for example, from the distal position in which the distal end 430 of the hammer head 430 is adjacent or in contact with the proximal end 450*a* of the adapter 450, as shown in FIG. 10C, to the intermediate position as shown in FIG. 10B, to the proximal position in which the proximal end 430*a* of the hammer head 430 is adjacent or in contact with an interior portion 446*a* of the edge 446, as shown in FIG. 10A.

An actuator, such as a magnetic linear actuator, can drive the rod 420 along the axis A1. The actuator, including any controller of the actuator, can be positioned on an exterior portion of the housing 410. For example, the actuator can be mounted to a proximal portion of the housing 410. Because the actuator is positioned outside the housing 410 and away from the rod 420 and/or the hammer head 430, the actuator is less susceptible to impacts which can damage the actuator. In some embodiments, the magnetic field produced by the magnetic linear actuator acts as a buffer or damper for the housing 410 and/or user. For example, in some implementations, an impact force experienced by the hammer head 430 and rod 420 (e.g., due to impacting the hammer housing 440) is substantially dampened and/or not transferred to the housing 410. In some embodiments, the amount of the impact force experienced by rod 420 that is transferred to the housing 410 is less than or equal to about: 10%, 20%, 30%, 40%, 50%, 60%, 70%, or otherwise.

Impact force can be controlled electronically based, for example, on the magnetic force applied to accelerate the magnetic rod 420. The force experienced by the housing 410 is, aside from frictional and other minor loses, equal and opposite to the magnetic forced applied to the rod 420, which can be substantially less than the impact force. In a normal mode of operation, the impact forces are only transmitted to the implement 460 and not the housing 410. The surgical impactor 400 can include a hard stop (e.g., a physical interference) to inhibit or prevent excessive displacement of the implement 460 with respect to the housing 410 by limiting total travel of the implement 460. In some implementations, once the implement 460 has reached a limit of travel, impact forces can be transmitted to the housing 410, which can limit further advancement of the implement 460. A dampening material between the hard stop and the housing 410, such as a plastic or a rubber material, may be incorporated to limit the instantaneous forces experienced by the housing 410.

In certain embodiments, the rod 420 substantially floats in the magnetic field produced by the magnetic linear actuator and/or substantially does not touch the inner walls of the housing 410. In various embodiments, the housing 410 does not provide a hard stop against movement of the rod 420 and/or does not have a physical interference in the axial direction through which impact force can be transmitted from the rod 420 to the housing 410.

The actuator can facilitate movement of the rod 420 in a proximal to distal direction and/or in distal to proximal direction as described herein. Driving the rod 420 in a proximal to distal direction along the axis A1 can cause the distal end 430*b* of the hammer head 430 to impact the proximal end 450*a* of the adapter 450. The frequency and force of the impact can be regulated by a controller of the surgical impactor 400. Driving the rod 420 in a distal to proximal direction along the axis A1 can cause the proximal end 430*a* of the hammer head 430 to impact the interior portion 446*a* of the edge 446. The impacts of the hammer head 430 with the hammer housing 440 and/or the adapter 450 can be transferred to, for example, the implement 460 or any other instrument attached to the adapter 450. The frequency, direction, and force of the impact can be controlled by a controller of the surgical impactor 400. In some embodiments, the controller can instruct the actuator to create a magnetic field to, for example, inhibit or prevent recoil when the hammer head 430 impacts the hammer housing 440 and/or the adapter 450. In some embodiments, the controller directs the linear actuator to control recoil force of the rod 420, such as by gradually slowing the rod 420. The controller can slow down or speed up the motion of the rod 420 over a period of time and/or distance. In various embodiments, the controller can use signals from sensors to calculate or otherwise determine impact force, rate of change or impact force, impact frequency, rod and/or hammer head displacement, rod and/or hammer head recoil, total applied force, and/or otherwise.

In some embodiments, the magnetic linear actuator can be a tubular linear motor as shown in FIGS. 3A and 3B. The magnetic linear actuator can include, in some embodiments, a u-channel linear motor, flat linear motor, voice coil actuator (VCA), moving coil actuator, solenoid, or otherwise. The actuator can include position sensors to detect and control the rod 420 along the housing 410, as well as other aspects.

The surgical impactor 400 can be configured to provide impact control. Various embodiments are configured to control impact energy, impact frequency, and/or impact direction. Some embodiments achieve impact control with direct electromagnetic linear actuation. Direct electromagnetic linear actuation allows for greater control over hammer stroke and force applied to accelerate the hammer. Variable stroke inherently allows for more optimal performance over a range of impact energies and frequencies. For a given hammer acceleration force, a longer stroke is required to achieve high energy and low frequency impacts, while a shorter stroke is required to achieve higher frequency and lower energy impacts. Electronic control of the impact parameters improves the user interface and simplifies potential integration with surgical robotics. The ability of the rod 420 to extend the full length of the lumen 415 allows for greater travel distance along the axis A1. This can beneficially allow for stronger impacts/strokes by the hammer head 430 as the rod 420 is allowed to travel a greater distance along the axis A1.

The surgical impactor 400 can provide enhanced ergonomics. The absence of a mechanism to convert rotary motion to linear motion can reduce the size and weight of the surgical impactor 400 and can improve form factor. The weight of the surgical impactor 400 can be reduced since the magnetic mass can contribute to the effective rod 420 mass. The surgical impactor 400 can avoid parasitic rotational inertia. Instead, substantially all inertia developed can be linear and can contribute to impact. Direct control over electromagnetic acceleration force of the rod 420 can smooth and limit recoil and vibration forces experienced by user.

The surgical impactor 400 can provide enhanced reliability. The simplification of the impact mechanism can improve reliability since there are fewer moving components that can potentially fail. The sudden impact forces experienced by the rod 420 are not transmitted back through a mechanism as would be the case with other rotary-to-linear mechanisms (e.g., ball screw, rack and pinion). While the magnetically actuated rod 420 has the potential to slide against stationary sidewalls (e.g., the interior surface of the lumen 415), there is little or no contact pressure between the sliding surfaces. This greatly improves any lubrication and sealing challenges typical of an autoclavable device. It may be possible for the sliding interface to be unsealed with periodic instrument milk lubrication (e.g., Miltex®). Minimal or reduced friction can improve the long-term consistency of the impact performance and/or prolongs the useful life of the device.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations. The term "vertical" refers to an orientation parallel to the Earth's gravity.

Conditional language, such as "can," "could," "might," or "may," unless specifically stated otherwise, or otherwise understood within the context as used, is generally intended to convey that certain examples include or do not include, certain features, element and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 100% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

Summary

Several illustrative examples of surgical impactors and related processes have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of the steps, processes, structures, and/or devices disclosed or illustrated in one example in this disclosure can be combined or used with (or instead of) any other portion of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The non-schematic figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated.

Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of surgical impactors and related processes have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

The following is claimed:

1. A surgical impactor comprising:
- a housing comprising a proximal end, a distal end, a cavity extending from the proximal end to the distal end, and a linear actuator;
- a rod comprising a proximal end and a distal end, the distal end comprising a first threading, wherein the rod is removably disposed inside the cavity of the housing;
- a hammer head on the distal end of the rod, the hammer head comprising a proximal end with a second threading;
- a hammer housing comprising a proximal end with a first opening, a distal end with a second opening, and a cavity disposed between the first and second openings; and
- an adapter comprising a proximal end and a distal end, wherein the proximal end of the adapter is attached to the distal end of the hammer housing;
- wherein the hammer head is inside the cavity of the hammer housing and is configured to move relative to the hammer housing;
- wherein the linear actuator is configured to move the rod, which causes the hammer head to move axially inside the hammer housing and to impact an inner surface of the hammer housing; and
- wherein the first threading and the second threading are configured to engage to connect the rod and the hammer head.

2. The surgical impactor of claim 1, wherein the distal end of the adapter is removably couplable to a surgical implement.

3. The surgical impactor of claim 2, wherein the surgical implement comprises one of a surgical nail and a surgical staple.

4. The surgical impactor of claim 1, further comprising one or more sensors.

5. The surgical impactor of claim 4, wherein the one or more sensors comprise at least one of an accelerometer, a force gauge sensor, and a displacement sensor.

6. The surgical impactor of claim 1, wherein the linear actuator comprises a magnetic linear actuator.

7. The surgical impactor of claim 1, wherein the linear actuator comprises at least one of a u-channel linear motor, a flat linear motor, a voice coil actuator (VCA), a moving coil actuator, and a solenoid.

8. The surgical impactor of claim 1, further comprising a controller configured to control operational settings of the surgical impactor, wherein the controller comprises a processor and a memory.

9. The surgical impactor of claim 8, wherein the operational settings of the surgical impactor comprise at least one of an impact frequency, an impact direction, and an impact force.

10. The surgical impactor of claim 1, wherein the hammer housing further comprises at least one window extending axially along the hammer housing, and wherein the hammer head is visible through the at least one window.

11. The surgical impactor of claim 1, further comprising a power source positioned on an exterior of the housing.

12. The surgical impactor of claim 11, wherein the power source comprises a battery.

13. The surgical impactor of claim 1, wherein an outer diameter of the hammer head is greater than an outer diameter of the proximal end of the rod.

14. The surgical impactor of claim 1, wherein the cavity of the housing is unobstructed when the rod is not disposed inside the cavity.

15. A surgical handpiece comprising:
- a grip,
- a trigger positioned along the grip,
- a barrel connected to the grip, the barrel comprising a cavity; and
- a surgical impactor positioned inside the cavity of the barrel, the surgical impactor comprising:
  - a housing comprising a through-lumen;
  - a rod positioned at least partially in the through-lumen;
  - a hammer head on an end of the rod;
  - a hammer housing configured to receive the hammer head, the hammer housing comprising a proximal end having an edge, wherein the edge is configured to block the hammer head from escaping the hammer housing in a proximal direction;
  - a linear actuator configured to move the rod relative to the housing and to dampen impact force from being transferred from the rod to the housing; and
  - an electronic controller configured to control operation of the linear actuator at least partly in response to actuation of the trigger.

16. The surgical handpiece of claim 15, wherein actuation of the trigger causes the hammer head to move axially in at least one of the proximal direction and a distal direction inside the hammer housing.

17. The surgical handpiece of claim 15, wherein the linear actuator comprises a magnetic linear actuator.

18. The surgical handpiece of claim 15, further comprising a controller configured to control operational settings of the surgical handpiece, wherein the controller comprises a processor and a memory.

19. The surgical handpiece of claim 18, wherein the operational settings of the surgical handpiece comprise at least one of an impact frequency, an impact direction, and an impact force.

20. The surgical handpiece of claim 15, wherein the hammer head is removably coupled to the end of the rod.

* * * * *